United States Patent [19]
Zaveri

[11] Patent Number: 5,958,437
[45] Date of Patent: Sep. 28, 1999

[54] DERMATOLOGICAL HEALING KIT, COMPONENTS THEREFOR, AND PROCESS FOR MAKING

[75] Inventor: Chanda Zaveri, Rancho Palos Verdes, Calif.

[73] Assignee: Geneda Corporation, Long Beach, Calif.

[21] Appl. No.: 09/022,808

[22] Filed: Feb. 12, 1998

Related U.S. Application Data

[63] Continuation-in-part of application No. 08/870,919, Jun. 6, 1997, abandoned.

[51] Int. Cl.$^6$ ....................................................... A61K 7/00
[52] U.S. Cl. .......................... 424/401; 424/62; 424/195.1; 514/873; 514/886; 514/887
[58] Field of Search .................................. 424/401, 195.1, 424/62; 514/887, 886, 873

[56] References Cited

U.S. PATENT DOCUMENTS 5,888,523  3/1999  Galask et al. ............................ 424/401

*Primary Examiner*—James M. Spear
*Attorney, Agent, or Firm*—Schweitzer Cornman Gross & Bondell LLP

[57] ABSTRACT

The invention is a dermatological healing kit having a pigment stabilizer component, and an antiinflammatory emollient component, and these components each by themselves, wherein the pigment stabilizer contains a mixture of glycerine, butylene glycol, bearberry extract, and mitracarpe extract; magnesium ascorbyl phosphate; and *tricholoma matsutake* singer; and the antiinflammatory emollient component contains *xanthoxylum bungeanum* planch; decarboxy camosine chlorhydrate; *polygonum multiforum* thumb; *rubus thunbergii* hance.cum spp.; and an aqueous mixture of *siegerbecka orientals* extract.

16 Claims, No Drawings ing and/or counteracting the darkening of skin faster than
DERMATOLOGICAL HEALING KIT, COMPONENTS THEREFOR, AND PROCESS FOR MAKING This application is a CIP of Ser. No. 08/870,919 filed Jun. 6, 1997 now abandoned.

FIELD OF THE INVENTION

The present invention relates to a dermatological healing kit of a pigment stabilizer component and an antiinflammatory emollient component, and to each of the components of the kit, and a process for making.

BACKGROUND OF THE INVENTION $CO_2$ lasers which were originally used in dermatological applications, emit a continuous beam having a wavelength of about 10,600 nm, in the mid-infrared portion of the electromagnetic spectrum. Laser energy is absorbed by biological tissue regardless of its pigmentation, due to the fact that the target of the beam is water which is the main component of the skin. The $CO_2$ laser destroys tissue by rapidly heating and vaporizing intracellular water. The conventional $CO_2$ laser also causes a large buildup of heat in the surrounding tissue as heat is conducted away from the irradiated site and thus the damage is not confined solely to that target site.

A newer development has been the use of the so called "resurfacing" $CO_2$ lasers which are used by dermatologists for the ablation of skin tissue generally for cosmetic purposes. The resurfacing $CO_2$ lasers deliver energy in much shorter bursts and within shorter periods of time, so that the heat conduction from the site of irradiation is substantially minimized. The resurfacing laser modifies the delivery of energy so that heat will not accumulate on, or conduct through to adjacent tissue, therefore, the lateral thermal damage is decreased. The water is rapidly vaporized from cellular tissues as an effect of the laser energy which creates a localized wound in somewhat of an "explosive" fashion, resulting in a skin condition similar to third degree burns. Each pass of the laser ablates approximately 50 to 100 μm of tissue. Complete ablation of tissue requires sufficient energy to vaporize the water contained in the tissue. If a sufficiently quick vaporization takes place, there is not enough time for an appreciable amount of heat conduction into surrounding tissue to cause thermal damage, but the delivered power density is sufficient to accelerate the rate of vaporization over the rate of heat conduction. Thus the ablation front travels faster than the thermal conduction front, resulting in somewhat less of a thermal injury, than with conventional $CO_2$ lasers.

Nevertheless, even the improved resurfacing laser technique results in a substantial inflammation of the skin with pronounced erythema, and in pronounced drying resulting in scaling and flaking of the skin, as well as a darkening of the skin due to the development of dark melanin pigmentation.

The dry, flaky and irritated skin which is the result of the moisture loss and of associated chemical insults, is due to biochemical and morphological changes in the stratum corneum of the dry skin. Much of the deterioration was found to be occasioned by the degradation of desmosomes in the lower layers of the stratum corneum, because they were found to rise to the surface during the laser attack, while being abnormally retained in the xerotic stratum corneum. Therefore, it was concluded that for the intercorneocyte cohesion is broken down desquamation which produces post-laser, and resulting in the degradation of the desmosomes by enzymes during the desquamation.

SUMMARY OF THE INVENTION

It is an object of the present invention to provide a kit containing component compositions for treating damage to and discolorations of laser-treated, ablated skin surfaces, and thus for the faster elimination of erythema from surface inflammation, for the moisturizing the skin, and for preventing and/or counteracting the darkening of skin faster than was heretofore possible.

It is another object of the present invention to provide a kit and its components for treating skin to be subjected to laser ablation surgery prior to the surgery, and also after the surgery to prevent, or minimize the occurrence of skin darkening as a result of the laser treatment, and to lighten the thus less darkened skin to its natural condition, as well as to treat the inflamed and otherwise damaged skin in a more systematic and rapid fashion than it was done heretofore.

Throughout the specification and the claims, all percentages are by weight, and all temperatures are given in centigrade. The ingredients are provided primarily by their CTFA names (of the Cosmetics, Toiletries and Fragrance Association's [CTFA] manual), and any available trade names are provided in the most comprehensive listing of each product, in parentheses following the CTFA name.

The present invention is based on the discovery that a dermatological healing kit, primarily suited for the healing of skin damaged by a resurfacing laser treatment, requires the application of a pigment stabilizer, and of an antiinflammatory emollient. The pigment stabilizer which can also be sold and used separately for that purpose alone, suitably has the following essential ingredients: (i) from about 1% to about 15%, more suitably from about 1% to about 10% a mixture of glycerin, butylene glycol, bearberry extract, and mitracarpus extract; (ii) from about 0.01% to about 1.5%, more suitably from about 0.01% to about 1% magnesium ascorbyl phosphate; and (iii) from about 0.01 to about 5%, more suitably from about 0.01% to about 1% *tricholoma matsutake* (Singer) extract. Optionally the pigment stabilizer can also contain the additional ingredients (vi) from about 5% to about 10%, more suitably from about 5% to about 8% of a mixture of dithiaoctanediol, gluconic acid, sutilains, and beta carotene; (v) from about 1% to about 9%, more suitably from about 5% to about 7% of a mixture of lecithin, and bearberry extract; and (vi) from about 10% to about 15%, more suitably from about 5% to about 6% ascorbyl methylsilanol pectinate.

The pigment stabilizer can optionally include the cosmetic adjuvants of (vii) from about 10% to about 46% an aqueous solution of lactobacillus/algae extract ferment; (viii) from about 10% to about 18% aloe barbadensis gel; (ix) from about 4% to about 10% of a mixture of licorice extract, asrergillus ferment, and ethoxydiglycol; (x) from about 4% to about 8% aqueous glycolic acid; (xi) from about 0.2% to about 4% a mixture of lecithin and xanthan gum; (xii) from about 0.1% to about 2.5% licorice extract; and (xiii) from about 0.5% to about 1.2% kojic acid.

A most suitable composition of the pigment stabilizer of the present invention contains (i) about 7.76% of a mixture of glycerin, butylene glycol, bearberry extract, and mitracarpus extract (Etioline); (ii) about 0.68% of magnesium ascorbyl phosphate (magnesium-L-ascorbyl-2-phosphate); (iii) about 0.68% of *tricholoma matsutake* (Singer) extract (song yi gel liquid 100%);, (iv) about 6.76% of a mixture of dithiaoctanediol, gluconic acid, sutilains, and beta carotene (melaclear-2); (v) about 6.76% of a mixture of lecithin, and bearberry extract (arbusomes); (vi) about 6.76% of ascorbyl methylsilanol pectinate (ascorbosilane C); (vii) about 33.78% of an aqueous solution of lactobacillus/algae extract ferment (sea acid); (viii) about 17.2% of aloe barbadensis gel (aloe-vera 1-1 FA); (ix) about 6.76% of a mixture of licorice extract, aspergillus ferment, and ethoxy-diglycol (gatuline whitening); (x) about 6.76% of aqueous glycolic acid (glycolic acid 70%); (xi) about 3.05% of a mixture of lecithin and xanthan gum (tensami 1/05); (xii) about 1.7% of licorice extract (licorice PT-40); and (xiii) about 1.35% kojic acid.

The antiinflammatory emollient of the present invention, which can also be used and sold apart from the kit for that purpose alone, suitably contains the essential ingredients (a) from about 3% to about 8%, more suitably from about 6.5% to about 7.5% zanthoxylum bungeanum; (b) from about 1% to about 6%, more suitably from about 4% to about 5% decarboxy carnosine HCl; (c) from about 1% to about 6%, more suitably from about 4% to about 5% polygonum multiforum (Thunb); (d) from about 1% to about 6% rubus thunbergii (Hance).cum spp.; and (e) from about 1% to about 5%, more suitably from about 2% to about 3% of an aqueous mixture of sigesbeckia orientalis extract.

The antiinflammatory emollient of the present invention can optionally include the further ingredients (k) from about 30% to about 50%, more suitably from about 45% to about 50% of a mixture of mineral oil, hydrogenated butylene/ ethylene/styrene terpolymer, and hydrogenated ethylene/ propylene/styrene terpolymer; (l) from about 1% to about 5%, more suitably from about 4% to about 5% of dimethylsilanol hyaluronate; (m) from about 0.5% to about 2%, more suitably from about 1.5% to about 2% sorbitol and yeast extract; (n) from about 1% to about 5%, more suitably from about 2% to about 3% of a mixture of PEG-60 hydrogenated castor oil, PEG-8 and ceramide 2; and (o) and from about 0.5% to about 2%, more suitably from about 1.5% to about 2% of an aqueous mixture of butylene glycol and chrysanthellum indicum extract.

The antiinflammatory emollient of the present invention can further include the cosmetic adjuvants (p) from about 1% to about 15% a mixture of cetearyl alcohol and ceteareth-20; (q) from about 1% to about 2% of a mixture of glyceryl stearate and PEG-100 stearate; (r) from about 0.05% to about 5% polysorbate-80; (s) from about 4% to about 6% methylsilanol mannuronate; (t) from about 3% to about 6% silanediol salicylate; (u) from about 2% to about 5% of a mixture of ethoxydiglycol, PEG-7 glyceryl cocoate; and centaurium enythnaea extract; (v) from about 2% to about 5% of an aqueous mixture of glycerin and lactobacillus/skeletonema ferment; (w) from about 1% to about 10% chitosan succinamide; and (x) from about 0.02% to about 1% of an extract of lonicera japonica with water.

Most suitably the antiinflammatory emollient of the present invention has the composition of (a) about 7.11% of zanthoxylum bungeanum (hua jiao); (b) about 4.7% of decarboxy carnosine chlorhydrate (alistin); (c) about 4.7% of polygonum multiforum (Thunb) (he shuo wu); (d) about 4.7% of rubus thunbergii (Hance).cum spp. (biao beng li); (e) about 2.36% of an aqueous mixture of sigesbeckia orientalis extract (siegerbecka); (f) about 46% of a mixture of mineral oil, hydrogenated butylene/ethylene/styrene terpolymer, and hydrogenated ethylene/propylene/styrene terpolymer (geahlene 200); (g) about 4.7% of an aqueous solution of dimethylsilanol hyaluronate (D.S.H.C.); (h) about 4.7% of sorbitol and yeast extract (drieline); (i) about 2.36% of a mixture of PEG-60 hydrogenated castor oil, PEG-8 and ceramide 2 (ceramide 2%); (j) about 1.66% of an aqueous mixture of butylene glycol and chrysanthellum indicum extract (lanachyrum-2B); (k) about 1% of a mixture of cetearyl alcohol 9Lnd ceteareth-20 (lipowax D); (l) about 2% of a mixture of glyceryl stearate and FPEG-100 stearate (arlacel 165); (m) about 1% of polysorbate-80 (tween 80); (n) about 4.7% of an aqueous solution of methylsilanetriol mannuronate (aligisium C); (o) about 2.36% of an aqueous solution of silanediol salicylate (D.S.B.C.); (p) about 2.36% of a mixture of ethoxydiglycol, PEG-7 glyceryl cocate, and centaurium erythraea extract (centarium); (q) about 2.36% of an aqueous mixture of glycerin and lactobacillus ferment and glyceryl skeletonema ferment (antoxine); (r) about 1.22% of chitosan succinamide (kitanami); and (s) about 0.01% of an extract of lonicera japonica with water (plantservative).

The antiinflammatory emollient of the present invention can be suitably prepared by combining none, some or all of the last above mentioned ingredients (e) through (s) at a temperature between about 45° C. and about 95° C., and either separately combining from none to all of the ingredients (a) through (d) at a temperature between about 30° C. and about 55° C. and then mixing them to the mixture of the ingredients (e) through (r), or mixing none or all of the ingredients (a) through (d) individually to the mixture of (e) through (r) at a temperature between about 30° C. and about 55° C. The aqueous loniceria japonica antibacterial and antiviral preservative is suitably added at an ambient temperature to the other compounded ingredients of the composition.

DETAILED DISCLOSURE

Experiments were carried out to determine which factors and to what extent influence the mechanism of thickened stratum corneum formation by the laser ablation, process and to determine what treatments would be effective for the depigmentation post laser pigmentation inhibition and reconstructively fading of the skin prior to and after laser treatment. The mechanisms and the serine proteases of skin ablation and their effect on stratum corneum desquamation were determined by zymographic techniques and cDNA cloning, followed by nucleotide sequence analysis and the resulting determination of the proteases and other enzymatic mechanisms in the stratum corneum. It was determined that laser ablation which results in a visible scab on the skin derives from a breakdown of the natural effect of the stratum corneum the major function of which is to protect the body against water loss and chemical insults. The stratum corneum adheres tightly to perform this function, but it is normally constantly renewed with a corresponding loss of individual cells from the surface. As a result normally the stratum corneum maintains a well regulated thickness, but it was found that the regulation of this thickness breaks down under the effect of the laser treatment.

The experiments for the determination of the enzymatic activities were conducted on stratum corneum sheets peeled from rhesus monkeys, and other kinds of stratum corneum obtained by successive tape stripping. The mechanism and rate of the stratum corneum sheet degradation was determined and the effects of various chemical ingredients were observed. The cloning of proteases and the expression of trypsin-like protease were made to determine nucleotide sequences to design degenerate PCR primers. Although stranded cDNAs were synthesized from mRNA derived from cultured human keratinocytes. cDNA inserts of plaque-purified isolates were subcloned for DNA sequencing, and the specific sense primers for trypsinogen I, II, III and IV were determined, and the antisense primer was also designed from consensus sequences.

The influence and the determination of the water content in a stratum corneum, and its influence on the effect of cosmetic ingredients on the degradation of desmosomal protein were carried out by experimental methods known per se. Cell dissociation from the stratum corneum was determined with various proteases, and desmosomal protein was detected in stratum corneum extracts. It was determined that lower water content resulted in the decrease of the degradation of desmosomal proteins, and a linear relationship was found between increase in water content in the stratum corneum and the digestion of desmosomes.

Stratum corneum sheets were treated before incubation, humectants were also added to the various cosmetic compositions and thus the effects of various cosmetic ingredients were determined in relation to the acceleration of the desmosonal digestion.

Various in vivo tests were carried on the ingredients of the components for their anti-inflammatory properties, as well as the effect on initial vasodilation and erythema were tested and interactive mechanisms were determined to check the ability to cancel out inflammatory phenomena either by direct action on enzymes, or by competitive phenoma. An example of the latter it was found in the post-laser application of the emollient composition present invention which cancelled out the effect of arachidonic acid by avoiding the occurrence of inflammatory phenomena after application.

There was no systematic approach in the prior art to these laser ablation phenomena, but the erythema and inflammation were typically ameliorated by topical antiinflammatories, such a steroids, however, these have constantly contributed to even further tissue degradation. The bad, dry skin condition was also treated in accordance with standard cosmetic practice with emollients and fats, such as vaseline and petrolatum.

The formation of dark melanin discoloration is quite similar to the dark patches of melasma, but in a continuous rather than demarcated blotchy macular manner. The known prior efforts have been concentrated on post-laser surgery treatment with known skin lighteners, such as hydroquinone with or without strong irritants, such as retinoic and/or azalezic acid. Hydroquinone was also combined with kojic acid. Beside their irritancy, these prior art hydroquinone-based compositions have also acted very slowly and were insufficient to bring about some skin lightening over a period of a few weeks, but requiring their application for periods of over 3 months.

The epidermis is often the first tissue layer to be affected by external aggression which in its simplest form manifests itself in vasodilation and erythema within a few minutes, usually followed by the development of edema in about less than an hour. The start of edema coincides with the development of cell infiltration. The inflammatory response is due to the formation of arachidonic acid metabolytes. It was experimentally determined that the repeatedly applied antiinflammatory emollient composition of the present invention cancels out the effects of arachidonic acid, resulting in a reduction and elimination of inflammatory phenomena. It was also found that the antiinflammatory emollient of the present invention also very strongly inhibits lipid peroxidation. The emollient of the present invention, furthermore also inhibits lipo oxygenase activity by providing a key enzyme in the synthesis of leukotrines which have an inflammation-mediating role.

Experiments also determined that the pigment stabilizer composition of the present invention is most suitably used both prior to, and after laser surgery. In its post-laser function, among others, the stabilized protease in the composition increases the ability of the epidermis better to resist the dissolution or peeling of its hardening layer by increasing keratolysis to promote shedding of the skin, and cell renewal. The keratase component also contributes to skin lightening, because it promotes diffusion and reinforces activity of inhibitors tending to prevent the neo-synthesis of melanin.

Various components of the pigment stabilizer of the present invention can temporarily, reversibly halt melanogenesis, to inhibit the regular production capacity of melanin; and can chelate copper. This contributes to inhibiting tyrosinase activity by depriving the enzyme of copper which otherwise contributes to melanin formation.

Post-laser treatment with the composition stops the further production of melanin and reduces a dark melanin component of the skin.

Various tests were carried out by dermatologists, comparing treatments of one side of laser-ablated faces with standard hydroquinone-containing compositions, the other halves of the faces were treated by the pigment stabilizer of the present invention. This resulted in a predictable lightening within about three weeks with a twice each day application of the present pigment stabilizer, whereas the known lighteners that included hydroquinone started to show a lightening effect only after about three months of treatment. The pigment stabilizer composition of the present invention also resulted in a 50% reduction in the extent of darkening, which very substantially contributed to the much shorter time required for returning to the natural skin color.

The pre-laser application of the present pigment stabilizer and the ingredients therein contribute to the formation of a colorless melanin variety, and also to the conversion of dark colored melanin variety to the colorless variety. This contributes to somewhat of a pre-laser lightening of the skin, but even more importantly to the reduction of the darkening variety form of melanin by converting it to the colorless form that contributes to the reduction of the darkening of the skin.

It was determined that the antiinflammatory moisturizer of the present invention stops itching within 2–3 days and erythema within 4–5 weeks.

The antiinflammatory emollient, composition of the present invention is an excellent moisturizer, but it would be to costly for daily cosmetic use. However, combined healing and emollient use can also be employed on otherwise damaged skin, such as a remedy for treating the aftereffects of burns, including sunburn, and of irritated skin.

The pigment stabilizer composition of the present invention can also be used as an improved general purpose skin lightener, or fading composition.

The ingredients of both compositions of the present inventions also provide a new and surprising synergistic effect.

Most suitably the pigment stablizer of the present invention contains the following ingredients in the following specified concentrations.

| % wt. | |
|---|---|
| 46.63 | Water |
| 8.6 | Aloe Barbadensis Gel |
| 8.59 | Lecithin |
| 5.94 | Ethoxydiglycol |
| 5.7 | Butylene Glycol |
| 4.73 | Glycolic Acid |
| 4.0 | Glycerin |

-continued

| % wt. | |
|---|---|
| 3.11 | Licorice (Glycyrrhiza Glabra) Extract |
| 2.7 | Dithiaoctanediol |
| 2.0 | Gluconic Acid |
| 1.39 | Sutilains |
| 1.35 | Kojic Acid |
| 1.06 | Xanthan Gum |
| 0.41 | Bearberry (Acrtostaphylos Uva-Ursi) Extract |
| 0.21 | Mitracarpus Extract |
| 0.41 | Aspergillus Ferment |
| 0.67 | Beta-Carotene |
| 0.78 | Lactobacillus/Algae Extract Ferment |
| 0.36 | Ascorbyl Methylsilanol Pectinate |
| 0.68 | Magnesium Ascorbyl Phosphate |
| 0.48 | Tricholoma Matsutake Extract |
| 0.2 | Propylene Glycol |

Most suitably the post-laser ablation moisturizer of the invention contains the following ingredients of the following specified concentrations:

| % wt. | |
|---|---|
| 43.0 | Mineral Oil |
| 30.15 | Water |
| 5.7 | Propylene Glycol |
| 4.6 | Sorbitol |
| 1.84 | Glycerin |
| 1.5 | Hydrogenated Butylene/Ethylene/Styrene Copolymer |
| 1.5 | Hydrogenated Ethylene/Propylene/Styrene Copolymer |
| 1.4 | PEG-60 Hydrogenated Castor Oil |
| 1.21 | Butylene Glycol |
| 1.1 | PEG-7 Glyceryl Cocoate |
| 0.05 | Dimethylsilanol Hyaluronate |
| 0.1 | Zanthoxylum Bungeanum Extract |
| 0.26 | Ceramide 2 |
| 0.02 | Lactobacillus/Skeletonema Ferment |
| 0.05 | Chrysanthellum Indicum Extract |
| 0.5 | Decarboxy Carnosine HCl |
| 0.4 | Polygonum Multiflorum Extract |
| 0.03 | Silanediol Salicylate |
| 0.1 | Rubus Parvifolius Extract |
| 0.13 | Chitosan Succinamide |
| 0.6 | Cetearyl Alcohol |
| 0.1 | Yeast Extract |
| 1.0 | PPG-2-Ceteareth-9 |
| 0.26 | Centaury (Centaurium Erythraea) Extract |
| 0.25 | Sigesbeckia Orientalis Extract |
| 0.01 | Honeysuckle (Lonicera Japonica) Extract |
| 1.0 | Glyceryl Stearate |
| 1.0 | Polysorbate 20 |
| 1.0 | PEG-100 Stearate |
| 0.4 | Ceateareth-20 |
| 0.7 | PEG-8 |

I claim:

1. A pigment stabilizer which comprises the ingredients: (i) from about 1% to about 15% a mixture of glycerine, butylene glycol, bearberry extract, and mitracarpus extract; (ii) from about 0.01% to about 1.5% magnesium ascorbyl phosphate; and (iii) from about 0.01 to about 5% *tricholoma matsutake* extract.

2. A dermatological healing kit the components of which comprise the pigment stabilizer of claim, and an antiinflammatory emollient.

3. The pigment stabilizer of claim 1, wherein said ingredients comprise (i) from about 1% to about 10% of a mixture of glycerine, butylene glycol, bearberry extract, and mitracarpus extract; (ii) from about 0.01% to about 1% Magnesium ascorbyl phosphate; and (iii) from about 0.01% to about 1% *tricholoma matsutake* extract.

4. The pigment stabilizer of claim 1, further comprising the ingredients: (i) from about 5% to about 10% of a mixture of dithiaoctanediol, gluconic acid, sutilains, and beta carotene; (ii) from about 1% to about 9% a mixture of lecithin, and bearberry extract; and (iii) from about 10% to about 15% ascorbyl methylsilanol pectinate.

5. The pigment stabilizer of claim 3, further comprising the ingredients: (i) from about 5% to about 8% a mixture of dithiaoctanediol, gluconic acid, sutilains, and beta carotene; (ii) from about 5% to about 7% of a mixture of lecithin, and bearberry extract; and (iii) from about 5% to about 6% ascorbyl methylsilanol pectinate.

6. The pigment stabilizer of claim 4, further comprising; the ingredients: (i) from about 10% to about 46% an aqueous solution of lactobacillus/algae extract ferment; (ii) from about 10% to about 18% aloe barbadensis gel; (iii) from about 4% to about 10% of a mixture of licorice extract, aspergillus ferment, and ethoxydiglycol; (iv) from about 4% to about 8% aqueous glycolic acid; (v) from about 0.2% to about 4% a mixture of lecithin and xanthan gum; (vi) from about 0.1% to about 2.5% licorice extract; and (vii) from about 0.5% to about 1.2% kojic acid.

7. A pigment stabilizer which comprises the ingredients: (i) about 7.76% of a mixture of glycerin, butylene glycol, bearberry extract, and mitracarpus extract; (ii) about 0.68% of magnesium ascorbyl phosphate; (iii) about 0.68% of tricholoma matsutake extract;, (iv) about 6.76% of a mixture of dithiaoctanediol, gluconic acid, sutilains, and beta carotene; (v) about 6.76% of a mixture of lecithin, and bearberry extract; (vi) about 6.76% of ascorbyl methylsilanol pectinate; (vii) about 33.78% of an aqueous solution of lactobacillus/algae extract ferment; (viii) about 17.2% of aloe barbadensis gel; (ix) about 6.76% of a mixture of licorice extract, aspergillus ferment, and ethoxydiglycol; (x) about 6.76% of aqueous glycolic acid; (xi) about 3.05% of a mixture of lecithin and xanthan gum; (xii) about 1.7% of licorice extract; and (xiii) about 1.35% kojic acid.

8. An antiinflammatory emollient which comprises the ingredients: (a) from about 3% to about 8% *zanthoxylum bungeanum*; (b) from about 1% to about 6% decarboxy carnosine HCl; (c) from about 1% to about 6% *polygonum multiforum*; (d) from about 1% to about 6% *rubus thunbergii*.cum spp.; and (e) from about 1% to about 5% an aqueous mixture of *sigesbeckia orientalis* extract.

9. The antiinflammatory emollient of claim 8, wherein said ingredients comprise (a) from about 6.5% to about 7.5% *xanthoxylum bungeanum*; (b) from about 4% to about 5% decarboxy carnosine HCl; (c) from about 4% to about 5% *polygonum multiforum*; (d) from about 4% to about 5% *rubus thunbergii*.cum spp.; and (e) from about 2% to about 3% an aqueous mixture of *siegesbekia orientalis* extract.

10. The antiinflammatory emollient of claim 8, further comprising the ingredients: (a) from about 30% to about 50% a mixture of mineral oil, hydrogenated butylene/ethylene/styrene terpolymer, and hydrogenated ethillene/propylene/styrene terpolymer; (b) from about 1% to about 5% dimethylsilanol hyaluronate; (c) from about 0.5% to about 2% sorbitol and yeast extract; (d) from about 1% to about 5% a mixture of PEG-60 hydrogenated castor oil, PEG-8 and ceramide 2; (e) and from about 0.5% to about 2% of an aqueous mixture of butylene glycol and chrysanthellum extract.

11. The antiinflammatory emollient of claim 10, wherein said ingredients comprise: (a) from about 45% to about 50% a mixture of mineral oil, hydrogenated butylene/ethylene/styrene terpolymer, and hydrogenated ethylene/propylene/styrene terpolymer; (b) from about 4% to about 5% dimethylsilanol hyaluronate; (c) from about 1.5% to about 2% sorbitol and yeast extract; (d) from about 2% to about 3% a mixture of PEG-60 hydrogenated castor oil, PEG-8 and ceramide 2; and (e) from about 1.5% to about 2% of an atqueous mixture of butylene glycol and chrysanthellum indicum extract.

12. The antiinflammatory emollient of claim 10, further comprising: (a) from about 1% to about 15% a mixture of cetearyl alcohol and ceteareth-20; (b) from about 1% to about 2% of a mixture of glyceryl stearate and PEG-100 stearate; (c) from about 0.05% to about 5% polysorbate-80; (d) from about 4% to about 6% methylsilanol mannuronate; (e) from about 3% to about 6% silanediol salicylate; (f) from about 2% to about 5% of a mixture of ethoxildiglycol, PEG-7 glyceryl cocoate, and *centaurium erythraea* extract; (g) from about 2% to about 5% of an aqueous mixture of glycerin and lactobacillus/skeletonerrma ferment; (h) from about 1% to about 10% chitosan succinamide; and (i) from about 0.02% to about 1% of an extract of *lonicera japonica* with water.

13. A antiinflammatory emollient which comprises the ingredients: (a) about 7.11% of *zanthoxylum bungeanum*; (b) about 4.7% of decarboxy carnosine HCl; (c) about 4.7% of *polygonum multiforum*; (d) about 4.7% of *rubus thunbergii-*.cum spp.; (e) about 2.36% of an aqueous mixture of *sigesbecka orientalis* extract; (f) about 46% of a mixture of mineral oil, hydrogenated butylene/ethylene/styrene terpolymer, and hydrogenated ethylene/propylene/styrene terpolymer; (g) about 4.7% of dimethylsilanol hyaluronate; (h) about 4.7% of sorbitol and yeast extract; (i) about 2.36% of a mixture of PEG-60 hydrogenated castor oil, PEG-8 and ceramide 2; (j) about 1.66% of an aqueous mixture of butylene glycol and chrysanthellum extract; (k) about 1% of a mixture of cetearyl alcohol and ceteareth-20; (l) about 2% of a mixture of glyceryl stearate and PEG-100 stearate; (m) about 1% of polysorbate-80; (n) about 4.7% of methylsilanol mannuronate; (o) about 2.36% of an aqueous solution of silanediol salicylate; (p) about 2.36% of a mixture of ethoxydiglycol, PEG-7 glyceryl cocoate, and centaurium erythraea extract; (q) about 2.36% of an aqueous mixture of glycerin and lactobacillus/skeletonema ferment and glyceryl skeletonema; (r) about 1.22% of chitosan succinamide; and (s) about 0.01% of an extract of *lonicera japonica* with water.

14. A process for preparing the antiinflammatory emollient of claim 8, which comprises mixing the ingredients (a) through (e) at a temperature between about 45° C. and about 95° C.

15. A process for preparing the antiinflammatory emollient of claim 10, which comprises mixing the further ingredients (b) through (e) with the ingredients (a) through (e) of claim 8 at a temperature between about 45° C. and about 95° C., and admixing the ingredient (a) to the resulting mixture. at a temperature between about 30° C. and about 55° C.

16. The dermatological healing kit of claim 2, wherein said antiinflammatory emollient comprises the ingredients: (a) from about 3% to about 8% *xanthoxylum bungeanum*; (b) from about 1% to about 6% decarboxy carnosine HCl; (c) from about 1% to about 6% *polygonum multiforum*; (d) from about 1% to about 6% *rubus thunbergii*.cum spp.; and (e) from about 1% to about 5% an aqueous mixture of *sigesbeckia orientalis* extract.

* * * * *